United States Patent [19]  
Loshaek

[11] 4,013,576  
[45] Mar. 22, 1977

[54] CONTACT LENS TREATING COMPOSITION
[75] Inventor: Samuel Loshaek, Chicago, Ill.
[73] Assignee: Wesley-Jessen Inc., Chicago, Ill.
[22] Filed: Nov. 21, 1973
[21] Appl. No.: 417,913
[52] U.S. Cl. .................................. 252/106; 21/58; 134/42; 252/542; 252/545; 252/547; 252/DIG. 7; 252/DIG. 14; 424/150; 424/316; 424/326; 424/329
[51] Int. Cl.² ...................... C11D 1/84; C11D 3/48
[58] Field of Search ............ 134/42; 252/106, 542, 252/546, 547, DIG. 14, DIG. 7, 545; 424/78, 329, 316; 260/501.12, 501.13; 21/2, 58

[56] References Cited  
UNITED STATES PATENTS

| | | | |
|---|---|---|---|
| 2,528,380 | 10/1950 | Mannheimer | 260/309.6 |
| 2,781,388 | 2/1957 | Mannheimer | 260/458 |
| 2,781,390 | 2/1957 | Mannheimer | 260/458 |
| 2,781,392 | 2/1957 | Mannheimer | 260/459 |
| 3,001,996 | 9/1961 | Mannheimer | 260/247.1 |
| 3,093,591 | 6/1963 | Freese | 252/106 |
| 3,156,656 | 11/1964 | Libby | 252/106 X |
| 3,171,752 | 3/1965 | Rankin | 106/194 |
| 3,341,460 | 9/1967 | Wei | 252/546 X |
| 3,394,174 | 7/1968 | Feigin | 260/509 |
| 3,549,747 | 12/1970 | Krezanoski et al. | 424/78 |
| 3,639,576 | 2/1972 | Kaspar et al. | 424/78 |
| 3,689,673 | 9/1972 | Phares | 424/326 |
| 3,755,561 | 8/1973 | Rankin | 424/78 |
| 3,767,788 | 10/1973 | Rankin | 424/78 |
| 3,882,036 | 5/1975 | Krezanoski et al. | 252/106 |

FOREIGN PATENTS OR APPLICATIONS  
1,231,541  5/1971  United Kingdom

OTHER PUBLICATIONS  
"The Miranol M Series," Miranol Chemical Co., New Jersey, 1958, pp. 2–4.

Primary Examiner—P.E. Willis, Jr.  
Attorney, Agent, or Firm—Pennie & Edmonds

[57] ABSTRACT

An improved contact lens treating composition is provided through the incorporation of an amphoteric surfactant as a detergent. The amphoteric surfactant provides good cleaning properties with no eye irritation and is stable in the presence of positively-charged bacteriocides in the composition.

7 Claims, No Drawings

CONTACT LENS TREATING COMPOSITION

BACKGROUND OF THE INVENTION

The present invention relates to improved contact lens solutions that are commonly employed with plastic contact lenses.

One purpose of such solutions is to provide an aqueous solution which will wet the relatively hydrophobic plastic surface, thereby conditioning it for easier and more comfortable insertion into the eye and more comfortable wear; i.e., a cushioning effect. The wetted surface is also more readily wetted by the tears in the eye thus reducing the occurrence of dry spots. Dry spots on the surface of a contact lens cause discomfort and visual interference.

Another purpose of a contact lens solution is to provide a soaking medium which contains an antibacterial agent or an antifungicide or both. The contact lens is left to soak in this medium when not in use, as for example, overnight.

Still another purpose of a contact lens solution is to provide a cleaning action to the surface of the contact lens. Contact lenses must be handled carefully to prevent scratches and deformation, yet they must be clean to retain good visual acuity. The cleaning action must, therefore, be provided under gentle conditions of handling.

Contact lens solutions have been developed which incorporate one or more of the foregoing characteristics of wetting, soaking, cushioning and cleaning, but these compositions of the prior art have deficiencies.

For example, benzalkonium chloride, a common broad-spectrum bacteriocide which gives the positively charged benzalkonium ion in aqueous media, cannot be incorporated in solutions that contain certain negatively-charged species, e.g., anionic surfactants, because the bacteriocide is precipitated out or otherwise inactivated as an antibacterial agent when the two materials are present in the same solution. This limits the use of what is otherwise a safe and effective antibacterial agent. Another deficiency in contact lens solutions is the lack of adequate cleaning action. Anionic surfactants which are efficient cleaners cannot be used in contact lens solutions containing positively-charged antibacterial agents because of the above-noted incompatibility. Another deficiency of the usual anionic or cationic surfactants is their tendency to irritate the eye. Additionally, such cationic surfactants tend to be hydrophobic and do not give the wetting necessary or desired.

SUMMARY OF THE INVENTION

The instant invention achieves proper lens treating solutions which will provide the improved cleaning, wetting, soaking and/or cushioning without eye irritation while, at the same time, being stable in the presence of and not inactivating positively charged bacteriocides. If a non-charged or otherwise non-antagonistic agent is used, then, of course, the other improved properties are still obtained.

Briefly stated, the present invention comprises a contact lens treating composition comprising water and an amphoteric molecule as the surfactant component in contact lens solutions. The term "amphoteric" surfactant as used herein, is one in which the functional part of the surfactant molecule contains both a negative and positive electronic charge. In its preferred embodiment, the composition also contains a positively charged bacteriocide.

DETAILED DESCRIPTION

The essential component of the composition is the surfactant which, as noted, must be an amphoteric molecule.

Thus, the non-amphoteric charged surfactant molecule consists of a relatively complex organic portion with a net positive or negative charge. The latter charge is balanced by a positive or negative counterion (e.g., $Na^+$, $Cl^-$) which is not connected to the molecule by a chemical bond but is held in its environment by the attraction between the oppositely charged moieties. In the amphoteric molecule, the complex organic portion referred to above contains both positive and negative charges (at least one of each). As with the singly-charged molecule, electrical neutrality is provided by counterions, both negative and positive counterions being required for the same molecule. The uncharged portion of the amphoteric molecule contains hydrophobic groups (the charged portions usually function as part of the hydrophilic groups) and may contain non-charged (i.e., nonionic) hydrophilic groups. The foregoing features of an amphoteric surfactant molecule are illustrated by the following chemical structure which is but one example of such a molecule:

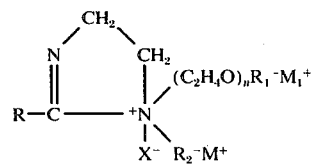

The structure is illustrated in the ionized form as it exists in aqueous media. In this structure, R represents a hydrophobic group and consists of an acid radical such as the fatty acid radicals of $C_6$-$C_{18}$ (coconut oil, lauric acid, capric acid, caprylic and ethylhexoic acid, oleic acid, linoleic acid and stearic acid); $R_2$ is

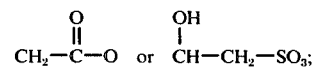

M and $M_1$ are cation salt forming groups, such as hydrogen or alkali metals, X is OH, or the acid group of an anionic surface active agent, e.g., sodium lauryl sulfate or sodium lauryl sulfonate; $R_1$ is H, or

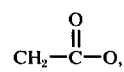

provided, however, when $R_1$ is hydrogen $M_1$ is absent; and $n$ is an integer from 1 to 40. Materials of this type are offered commercially under the trade name "Miranol". Typical examples of ionized amphoteric salts (commercial trade names Mironal 2MCA and C2M, respectively) are shown below:

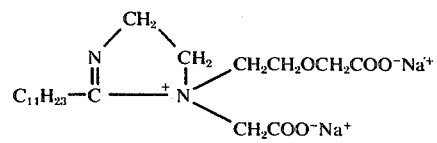

-continued

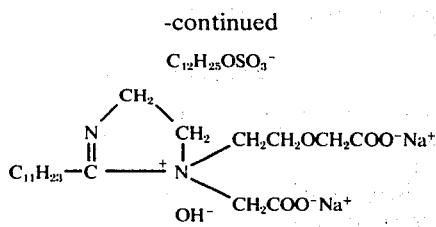

Broadly, these compounds can be monocarboxylates, dicarboxylates, or sulfonates. The counterions in the first example are $Na^+$ and $C_{12}H_{25}OSO_3^-$ and in the second example $Na^+$ and $OH^-$.

Another class of amphoteric surfactants is given by the following chemical structure in the ionized form:

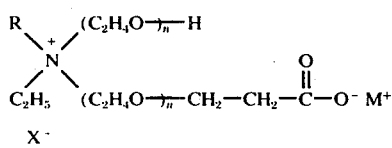

where, R is a hydrophobe radical such as methyl octadecyl, methyldodecyl, methyl octadecenyl, etc.; M is an alkali metal, such as Na, K, etc.; X is the negative part of a quaternizing agent, such as $CH_3OSO_3$, $C_2H_5OSO_3$, Cl Br, etc., n is an integer from 1 to 40. Materials of this type are available commercially under the trade name Sanac. This molecule has a non-ionic functionality, $(C_2H_4O)_nH$. Specific examples are [2-(2-carboxyethyl) ethyl], (2-hydroxyethyl) methyloctadecylammonium methyl sulfate, potassium salt; [2-(2-carboxyethoxy) ethyl] 2-[2-(hydroxyethoxy) ethoxyethyl] methyloctadecenylammonium methyl sulfate, potassium salt; and [2-(2-carboxyethoxy) ethyl] 2-(2-hydroxyethoxy) ethoxyethyl] methyldodecylammonium methyl sulfate, potassium salt. Another class of amphoteric surfactants with non-ionic functionality may be exemplified by the following chemical structure, in the ionized form:

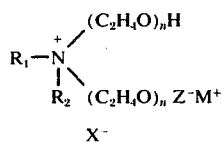

where $R_1$ is a fatty acid radical or other hydrophobe radical, $R_2$ is an alkyl or substituted alkyl radical, Z is a sulfate or sulfonic group, e.g., $-SO_4$, $-CH_2CH_2-SO_3$; M is an alkali metal such as Na or K; X is the negative radical from a quaternizing reagent such as $CH_3OSO_3$, $C_2H_5OSO_3$, Cl, Br, etc.

The particular amphoteric surfactant is not the subject of the present invention, but rather the use of such a surfactant in contact lens formulations to be illustrated in the following examples. The surfactant purity must be adequate so that impurities introduced during synthesis and not removed, do not react adversely or antagonistically with antibacterial agents or other ingredients.

As to bacteriocide used, positively-charged bacteriocides such as alkylbenzyldimethylammonium chloride (benzalkonium chloride) are preferred. Equally suitable are other bacteriocides commonly used in contact lens solutions such as sodium ethylmercurithiosalicylate (Thimerosal), nonylphenoxypolyethoxyethanol-iodine complex (Biopal), and 1,1'-hexamethylene bis[5-(p-chlorophenyl) biguanide] (chlorhexidine). The amount of bacteriocide used is that required to give the most effective antibacterial effect and will vary dependent upon the bacteriocide used. Preferably, the bacteriocide is added in an amount of from about 0.01 to about 0.015% by weight of the total solution.

Other materials that can be added for their usual effect are the standard buffering agents, preferably phosphate buffers, to buffer the pH of the composition to about pH 7, a tonicity agent (physiological saline) to adjust tonicity to that of the human eye, the usual chelating agents such as the sodium salt of ethylene diamine tetraacetic acid which act with the bacteriocides to enhance their effect, and wetting components such as methyl cellulose, polyvinyl alcohol, and polyvinyl pyrrolidone to help condition the contact lens and make it more comfortable to wear. Certain of these wetting components also act to control the viscosity of the solution. All of these materials are added in their usual amounts for their usual effects.

The amphoteric surfactant is used in an amount less than about 1% by weight of the composition, and, preferably, between about 0.1 and 0.5% by weight.

As to water used in the composition, it is preferred to use distilled water.

With certain combinations of bacteriocide and surfactant, there may be some lack of stability of the solution upon prolonged storage. This has been found to be particularly true with respect to combinations of Miranol and Benzalkonium chloride. Thus, while operative, the combination of these two materials would not be as suitable for prolonged storage since toward the end of such prolonged time, the anti-bacterial agent may be precipitated out of the solution otherwise inactivated.

The invention will be described in connection with the following examples which are set forth for purposes of illustration only and in which the amount of each component is in percent by weight.

|  | EXAMPLES | | | | | |
|---|---|---|---|---|---|---|
|  | 1 | 2 | 3 | 4 | 5 | 6 |
| Methocel | 0.500 | 0.500 | 0.500 | 0.500 | 0.500 | 0.500 |
| Polyvinyl alcohol[1] | 1.000 | 1.000 | 1.000 | 1.000 | 1.000 | 1.000 |
| Distilled water | 97.435 | 97.440 | 97.335 | 97.340 | 97.335 | 97.340 |
| Phosphate buffer[2] | 0.300 | 0.300 | 0.300 | 0.300 | 0.300 | 0.300 |
| Sodium chloride | 0.650 | 0.650 | 0.650 | 0.650 | 0.650 | 0.650 |
| Sodium salt of EDTA | 0.005 | 0.005 | 0.005 | 0.005 | 0.005 | 0.005 |
| Benzalkonium chloride | 0.010 | — | 0.010 | — | 0.010 | — |
| Thimerosal | — | 0.005 | — | 0.005 | — | 0.005 |
| Miranol C2M-SF conc.[3] | — | — | 0.200 | 0.200 | — | — |
| Sanac C[4] | — | — | — | — | 0.300 | 0.300 |

-continued

| | EXAMPLES | | | | | |
|---|---|---|---|---|---|---|
| | 1 | 2 | 3 | 4 | 5 | 6 |
| Nonionic surfactant[5] | 0.100 | 0.100 | — | — | — | — |

[1]87.2–89.2% hydrolysis; Viscosity: 21–25 cp (4% aqueous solution at 20° C.).
[2]Sodium dihydrogen phosphate and disodium hydrogen phosphate.
[3]Formula:

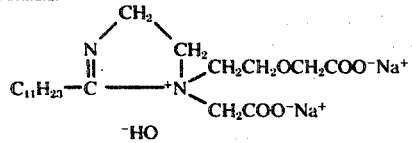

[4][2-(2-Carboxyethoxy)ethyl][2-(2-Hydroxyethoxy)Ethoxyethyl]Methyldodecyl-ammonium Methyl Sulfate, Potassium Salt.
[5]Nonylphenoxy polyethoxy ethanol.

In the foregoing examples, Examples 1 and 2 are controls and Examples 3 to 6 are trifunctional solutions of the present invention which clean, wet, and soak and which are on the lens and go onto the eye of the user when the lens is inserted onto the eye. The controls caused a stinging sensation in the eye, whereas the compositions of Examples 3 to 6 did not, and the controls did not clean and were less "comfortable" than the solutions of Examples 3 to 6.

While the invention has been described in connection with a preferred embodiment, it is not intended to limit the invention to the particular form set forth, but, on the contrary, it is intended to cover such alternatives, modifications and equivalents as may be included within the spirit and scope of the invention as defined by the appended claims.

What is claimed is:

1. A substantially isotonic contact lens treating solution consisting essentially of water, a bacteriocide that is non-irritating to the human eye, and a quaternary ammonium amphoteric surfactant selected from:

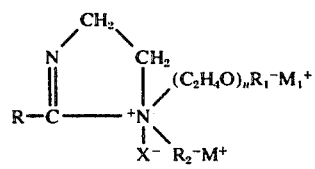

in which R is a $C_6$-$C_{18}$ fatty acid radical; $R_2$ is

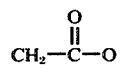

or

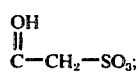

M and $M_1$ are alkali metals; X is OH or a sulfate or sulfonate acid group of an anionic surface active agent; $R_1$ is H or

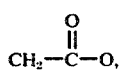

provided, however, when $R_1$ is hydrogen, $M_1$ is absent; and n is an integer from 1 to 40;

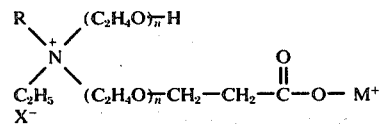

in which R is a hydrophobe $C_6$-$C_{19}$ hydrocarbon radical; M is an alkali metal; X is a lower alkyl sulfate group or halide; and n is an integer from 1 to 40; and

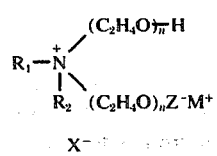

in which $R_1$ is a $C_6$-$C_{18}$ fatty acid radical, $R_2$ is a $C_1$-$C_4$ alkyl; Z is a sulfate or sulfonate group; M is an alkali metal radical; and X is a lower alkyl sulfate group or halide, said solution having a pH of about 7; said amphoteric surfactant being present in an effective amount but no more than about 1% by weight, and said bacteriocide being present in an amount between approximately 0.01% and 0.015% by weight.

2. The solution of claim 1 wherein the surfactant is selected from [2-(2-carboxyethyl) ethyl], (2-hydroxyethyl) methyloctadecylammonium methyl sulfate, potassium salt; [2-(2-carboxyethoxy) ethyl] 2-[2-(hydroxyethoxy) ethoxyethyl] methyloctadecenylammonium methyl sulfate, potassium salt; and [2-(2-carboxyethoxy) ethyl] 2-[2-(2-hydroxyethoxy) ethoxyethyl] methyldodecylammonium methyl sulfate, potassium salt.

3. A solution according to claim 1 in which the acid group of an anionic surface-active agent in the heterocyclic compound is a lauryl sulfate or sulfonate group.

4. A substantially isotonic contact lens treating solution according to claim 2 in which the bacteriocide is benzalkonium chloride.

5. A substantially isotonic contact lens treating solution consisting essentially of water, a bacteriocide that is non-irritating to the human eye selected from an alkylbenzyldimethylammonium chloride, sodium ethylmercurithiosalicylate, nonylphenoxy polyethoxyethanol-iodine complex or chlorohexidine, and a quaternary ammonium amphoteric sufactant selected from:

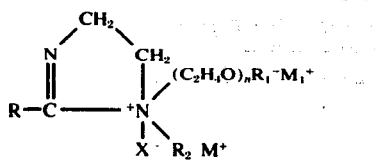

in which R is a $C_6$-$C_{18}$ fatty acid radical; $R_2$ is

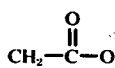

or

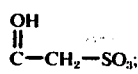

M and $M_1$ are alkali metals; X is OH or a sulfate or sulfonate acid group of an anionic surface active agent; $R_1$ is H or

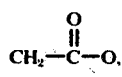

provided, however, when $R_1$ is hydrogen, $M_1$ is absent; and $n$ is an integer from 1 to 40;

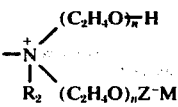

in which R is a hydrophobe $C_6$-$C_{19}$ hydrocarbon radical; M is an alkali metal; X is a lower alkyl sulfate group or halide; and $n$ is an integer from 1 to 40; and $$R_1-\overset{+}{N}\begin{matrix}(C_2H_4O)_{\overline{n}}H \\ \\ R_2 \quad (C_2H_4O)_nZ^-M^+\end{matrix}$$

$X^-$ in which $R_1$ is a $c_6$-$C_{18}$ fatty acid radical; $R_2$ is a $C_1$-$C_4$ alkyl; Z is a sulfate or sulfonate group; M is an alkali metal radical; and X is a lower alkyl sulfate group or halide, said solution having a pH of about 7; said amphoteric surfactant being present in an effective amount but no more than about 1% by weight, and said bacteriocide being present in an amount between approximately 0.01% and 0.015% by weight.

6. The method of treating contact lenses which comprises immersing them in the solution of claim 1 for a time sufficient to clean, wet, and soak the lenses, and then removing the lenses from the solution and placing them in the eyes of the user.

7. The method of treating contact lenses which comprises immersing them in the solution of claim 2 for a time sufficient to clean, wet, and soak the lenses, and then removing the lenses from the solution and placing them immediately in the eyes of the user.

* * * * *